United States Patent
Chen et al.

(10) Patent No.: US 12,350,249 B2
(45) Date of Patent: Jul. 8, 2025

(54) EFFICIENT ANTI-BACTERIAL HYDROXY ACID ESTER OLIGOMER

(71) Applicant: NANJING BIOSERICA ERA BIOLOGICAL TECHNOLOGY CO., LTD., Jiangsu (CN)

(72) Inventors: Xuejun Chen, Hangzhou (CN); Guomin Zhou, Hangzhou (CN)

(73) Assignees: NANJING BIOSERICA ERA ANTIMICROBIAL MATERIALS TECHNOLOGY GROUP CO., LTD., Nanjing (CN); NANJING YUANJIAN BIOTECHNOLOGY CO., LTD., Nanjing (CN)

( * ) Notice: Subject to any disclaimer, the term of this patent is extended or adjusted under 35 U.S.C. 154(b) by 0 days.

(21) Appl. No.: 18/378,480

(22) Filed: Oct. 10, 2023

(65) Prior Publication Data

US 2024/0082201 A1    Mar. 14, 2024

Related U.S. Application Data

(63) Continuation of application No. 17/510,375, filed on Oct. 25, 2021.

(30) Foreign Application Priority Data

Oct. 26, 2020 (CN) .......................... 202011155869.5
Sep. 27, 2021 (CN) .......................... 202111137059.1

(51) Int. Cl.
*A61K 31/22* (2006.01)
*A61P 31/04* (2006.01)
*C07C 69/675* (2006.01)
*C07C 69/68* (2006.01)

(52) U.S. Cl.
CPC .................................. *A61K 31/22* (2013.01)

(58) Field of Classification Search
CPC ....... C07C 69/675; C07C 67/68; A61K 31/22; A61P 31/04
See application file for complete search history.

(56) References Cited

U.S. PATENT DOCUMENTS

| 5,563,239 A | 10/1996 | Hubbs et al. |
| 2015/0038391 A1 | 2/2015 | De Wit et al. |
| 2017/0196826 A1 | 7/2017 | Pirttila et al. |

FOREIGN PATENT DOCUMENTS

| CN | 110452115 A | 11/2019 |
| CN | 113200849 A | 8/2021 |
| KR | 20150054151 A | 5/2015 |
| WO | 2019/213833 A1 | 11/2019 |

OTHER PUBLICATIONS

Snoch et al. Catalysis 2019, 9, 510, p. 1-12, published Jun. 5, 2019.*
Bansal et al. Drug Research 2014, 64, 240-245.
Bachmann et al. Helv Chim Acta 1998, 81, 2430-2461.
Ma L, Zhang Z, Li J, Yang X, Fei B, Leung PHM, Tao X. A New Antimicrobial Agent: Poly (3-hydroxybutyric acid) Oligomer. Macromol Biosci. May 2019; 19(5):e1800432. doi: 10.1002/mabi.201800432. Epub Apr. 5, 2019. PMID: 30951260.
Kia Bo, WU Qi. Lipase-catalyzed synthesis of R-Poly (3-hydroxybutyrate) oligomer[J]. Journal of Zhejiang University (Science Edition), 2018, 45(1): 112-117. DOI: 10.3785/j.issn.1008-9497.2018.01.016.

* cited by examiner

*Primary Examiner* — Irina Neagu
(74) *Attorney, Agent, or Firm* — Oliff PLC

(57) ABSTRACT

An efficient anti-bacterial hydroxy acid ester oligomer of the present invention has a general structural formula (I). Starting from the design of molecular structure, the present invention rationally designs the end group and chain length structure of the substance of formula (I), and controls its c log P value, so that the substance of formula (I) of the present invention reaches an appropriate size, which maximizes the ability of the substance of formula (I) to penetrate into the bacteria and destroy the bacterial cell membrane, thereby achieving high anti-bacterial efficiency. By precisely designing the molecular structure, the present invention regulates the hydrophilicity and hydrophobicity of the hydroxy acid ester oligomer to obtain a bio-based anti-bacterial agent with controllable water solubility.

3 Claims, 3 Drawing Sheets

EFFICIENT ANTI-BACTERIAL HYDROXY ACID ESTER OLIGOMER

CROSS REFERENCE OF RELATED APPLICATION

This is a continuation of application Ser. No. 17/510,375 filed Oct. 25, 2021 which claims priority under 35 U.S.C. 119(a-d) to CN 202111137059.1, filed Sep. 27, 2021, and CN202011155869.5, filed Oct. 26, 2020.

BACKGROUND OF THE PRESENT INVENTION

Field of Invention

The present invention relates to a technical field of biomedicine, and more particularly to an efficient anti-bacterial hydroxy acid ester oligomer.

Description of Related Arts

Anti-bacterial agents refer to substances which keep the growth or reproduction of certain microorganisms (bacteria, fungi, yeasts, algae, viruses, etc.) below a certain level within a certain period of time. Anti-bacterial agents are widely used in textiles, plastics, detergents, medical supplies and other fields.

With the continuous improvement of living standards, the hygienic requirements for textiles and various household plastics are also getting higher and higher. The continuous improvement of natural and environmental protection standards for anti-bacterial products is of great practical importance for developing the health care level of a country and reducing cross-infection in the public environment. Therefore, it is imperative to do research on natural, safe and efficient anti-bacterial agents for bio-based materials.

Chinese patent CN110452115A disclosed a poly-3-hydroxybutyrate oligomer, which is used to prepare anti-bacterial materials. The minimum inhibitory concentration (MIC, unit mg/mL) is as follows:

| S. aureus | K. pneumoniae | C. albicans |
|---|---|---|
| 6.25 | 12.5 | 25 |

The anti-bacterial activity of the above-mentioned oligomers is not high enough to meet the growing performance requirements for anti-bacterial products; and water solubility of the above-mentioned oligomers is not adjustable, resulting in a narrow application range. In addition, the raw materials used in the synthesis process are expensive and are not biological-based material butyrolactone. Toxic catalysts and solvents are also used, resulting in complicated post-treatment processes.

Because bacteria have a highly organized cell membrane structure, they can effectively resist the combination and penetration of foreign invading molecules. Therefore, rational design of the anti-bacterial agents that effectively penetrate and destroy bacterial cell membranes is of great significance. The present invention is based on long-term research, which shows that the use of the synergistic effect of the end groups and chain lengths of hydroxy acid ester oligomers can effectively improve the efficiency of the anti-bacterial agent during penetrating and destroying bacterial cell membranes, thereby achieving high anti-bacterial efficiency, and further achieving controllable water solubility of the anti-bacterial agent.

SUMMARY OF THE PRESENT INVENTION

Based on development demand for natural and eco-friendly anti-bacterial agents, an object of the present invention is to provide an efficient anti-bacterial substance R-(−)-hydroxy acid ester oligomer.

The anti-bacterial substance R-(−)-hydroxy acid ester oligomer of the present invention has a pH value of nearly neutral, and has a general structural formula (I):

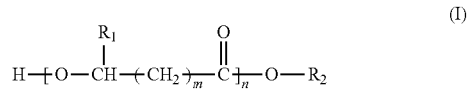

wherein n is a natural number of 1-8; $R_1$ is a $C_1$-$C_5$ alkyl group; $R_2$ is a $C_2$-$C_8$ alkyl group; m is a natural number of 0-3.

wherein n is a natural number of 1-8, which means a degree of polymerization DP is 1-8; $R_1$ is a $C_1$-$C_5$ alkyl group, preferably a $C_1$-$C_2$ alkyl group; $R_2$ is a $C_2$-$C_8$ alkyl group, preferably $C_5$-$C_6$ alkyl group; m is a natural number of 0-3, preferably m is 0 or 1.

Preferably, a c log P value of the efficient anti-bacterial hydroxy acid ester oligomer is 1.5-3.0; more preferably 2.0-2.5.

Preferably, the efficient anti-bacterial hydroxy acid ester oligomer has a general structural formula (II) or (III):

Preferably, in the general structural formula (I), when n=1-3, $R_1$ is the $C_1$-$C_5$ alkyl group, $R_2$ is a $C_2$-$C_3$ alkyl group, and m=0-3, the R-(−)-hydroxy acid ester oligomer is a water-soluble substance. In the general structural formula (I), when n=1-3, $R_1$ is the $C_1$-$C_5$ alkyl group, $R_2$ is a $C_4$-$C_8$ alkyl group, and m=0-3, the R-(−)-hydroxy acid ester oligomer is a water-insoluble substance which is soluble in a variety of organic solvents (such as ethanol, n-butanol, dimethyl sulfoxide, acetone, ether). In the general structural formula (I), when n=4-8, $R_1$ is the $C_1$-$C_5$ alkyl group, $R_2$ is the $C_2$-$C_8$ alkyl group, and m=0-3, the R-(−)-hydroxy acid ester oligomer is a water-insoluble substance which is soluble in a variety of organic solvents (such as ethanol, n-butanol, dimethyl sulfoxide, acetone, ether).

Preferably, the water-soluble substance R-(-)-hydroxy acid ester oligomer has a general structural formula (IV):

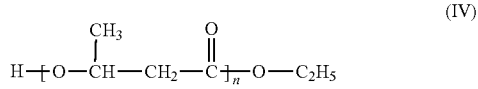

wherein n=2-3.

Preferably, the water-insoluble substance R-(-)-hydroxy acid ester oligomer having a general structural formula (V):

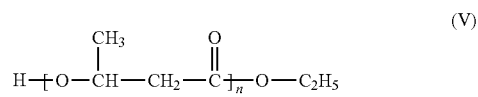

wherein n=4-8.

Beneficial effects of the present invention are as follows.

1. Starting from the design of molecular structure, the present invention rationally designs the end group and chain length structure of the substance of formula (I), and controls its c log P value, so that the substance of formula (I) of the present invention reaches an appropriate size, which maximizes the ability of the substance of formula (I) to penetrate into the bacteria and destroy the bacterial cell membrane, thereby achieving high anti-bacterial efficiency.

2. By precisely designing the molecular structure, the present invention regulates the hydrophilicity and hydrophobicity of the R-(-)-hydroxy acid ester oligomer to obtain a bio-based anti-bacterial agent with controllable water solubility, which broadens application range such as food, medicine, and cosmetics. When anti-bacterial agents with good water solubility, convenient use and uniform dispersion of substances in water are required, the water-soluble hydroxy acid ester oligomer can better satisfy the utilization needs. When coatings, fibers, plastics, building materials and other fields require water-resistant anti-bacterial agents to ensure a long-lasting anti-bacterial effect, only water-insoluble hydroxy acid ester oligomer can meet the demands.

3. The raw materials used in the present invention are all bio-based raw ones, which are convenient and easy to obtain; toxic catalysts and solvents are avoided in the synthesis process, which means no complicated post-processing is needed, and the catalyst can be recycled. The present invention is conducive to scaling up and producing, and is also conducive to meeting environmental protection requirements and reducing production costs.

DETAILED DESCRIPTION OF THE PREFERRED EMBODIMENT

The technical solutions and effects of the present invention will be further described below in conjunction with the embodiments. However, the present invention is not limited to the materials, proportions and methods shown in the embodiments. Any changes that can be easily obtained by those skilled in the art based on the material combinations and methods shown in these embodiments belong to the protection scope of the present invention.

Embodiment 1: Synthesis of R-(-)-3-hydroxybutyrate Ethyl Ester Oligomer

Embodiment 1-1

Adding 10 g of 3-hydroxybutyrate ethyl ester and 0.01 g of zinc acetate (i.e. a mass ratio of 3-hydroxybutyrate ethyl ester is 0.1%) in a three-necked flask with mechanical stirring, a thermometer and a distillation device, wherein a stirring speed is approximately 150 revolutions; under an environment with a trace of nitrogen, increasing a temperature to 150° C. with a speed of 0.5-3° C./min to react for 1 hour, then stopping reaction to obtain a 3-HB oligomer; detecting a degree of polymerization by a mass spectrometry, wherein an anti-bacterial experiment refers to *GB/T 20944.3-2008 Textiles-Evaluation for anti-bacterial activity-Part 3: Shake flask method*, a strain used is *Escherichia coli* ATCC 25922.

Embodiments 1-2 and 1-3

According to Table 1, catalyst types and reaction temperatures are changed on the basis of the embodiment 1-1, while other conditions are the same as those of the embodiment 1-1 to obtain the R-(-)-3-hydroxybutyrate ethyl ester oligomers with different polymerization degrees.

TABLE 1

Experimental conditions and product parameters of embodiments 1-1, 1-2 and 1-3

| Catalyst | Reaction temperature (° C.) | Reaction time (h) | Degree of polymerization (n) | Solubility | Purity | Anti-bacterial rate (%) |
|---|---|---|---|---|---|---|
| 1-1 0.1% zinc acetate | 150 | 1 | 2-3 | water-soluble | 100% | 99 |
| 1-2 0.1% zinc acetate | 200 | 2 | 4-8 | water-insoluble | 100% | 99 |
| 1-3 0.1% tetrabutyl titanate | 150 | 1 | 2-3 | water-soluble | 100% | 99 |

Figure 1:
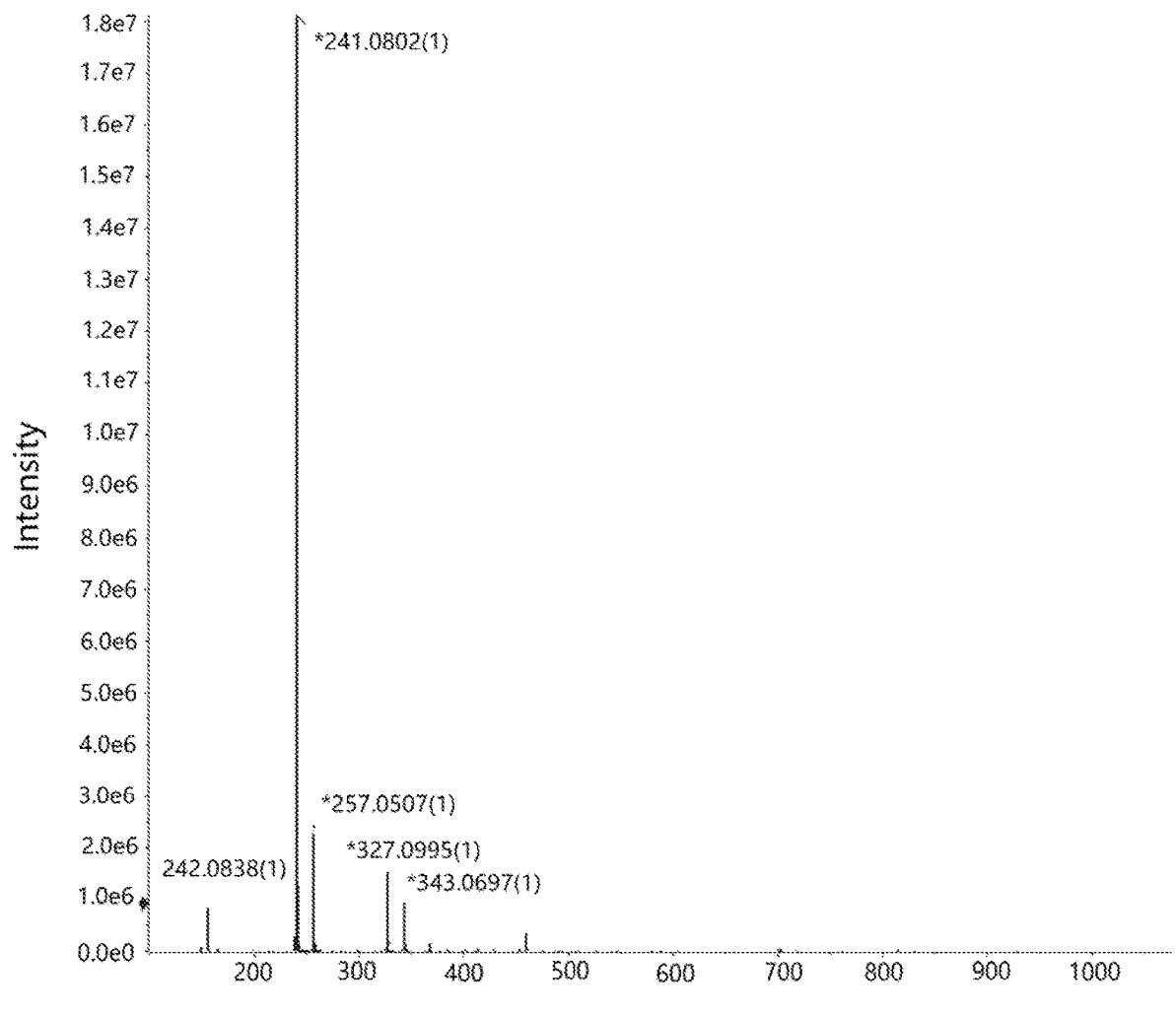
FIG. 1 is a mass spectrometry result of a water-soluble R-(-)-3-hydroxybutyrate ethyl ester oligomer according to embodiment 1-1.

FIG. 1 is a mass spectrometry result of a water-soluble R-(−)-3-hydroxybutyrate ethyl ester oligomer according to embodiment 1-1.

Figure 2:
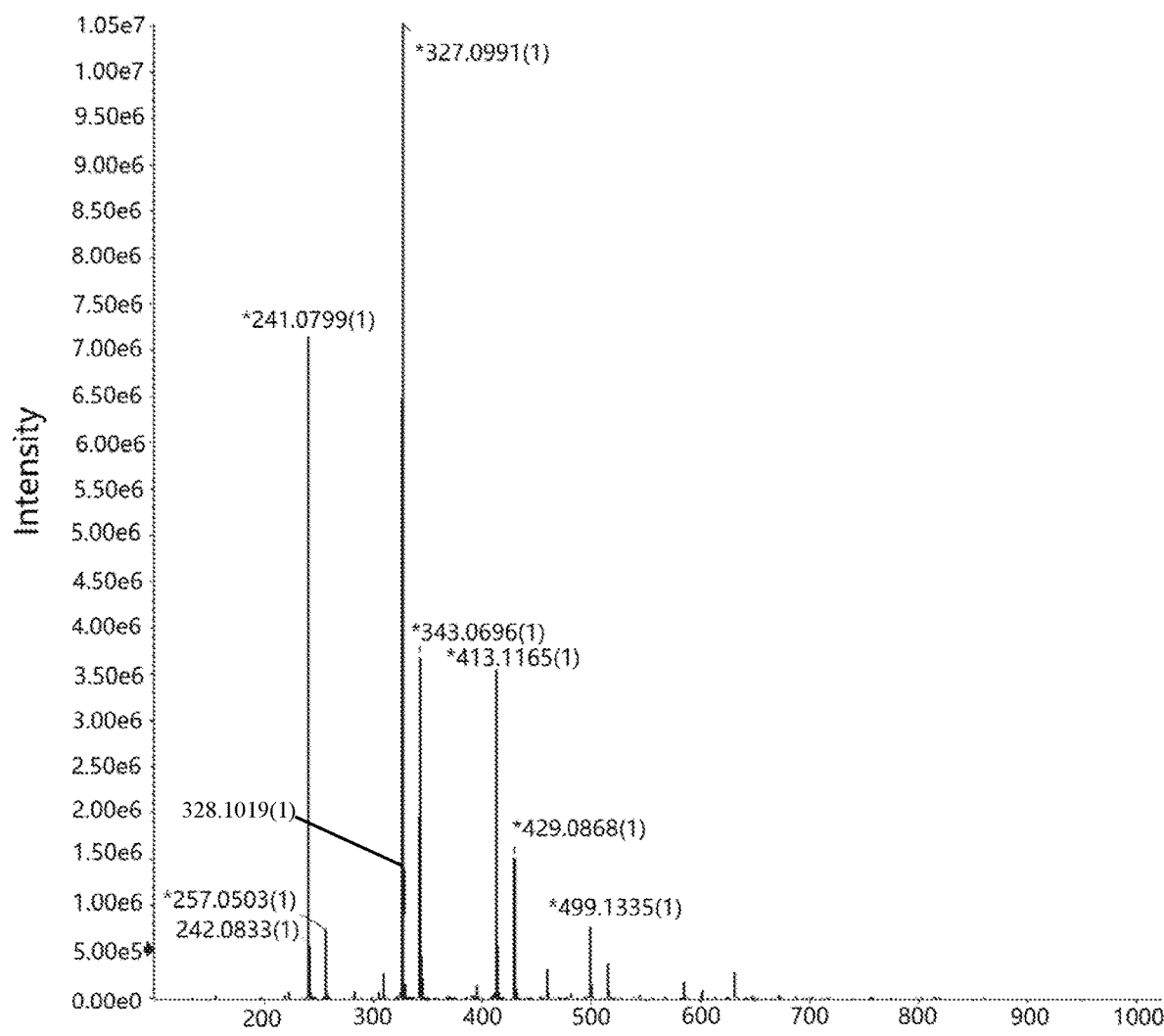
FIG. 2 is a mass spectrometry result of a water-insoluble R-(-)-3-hydroxybutyrate ethyl ester oligomer embodiment 1-2.

FIG. 2 is a mass spectrometry result of a water-insoluble R-(−)-3-hydroxybutyrate ethyl ester oligomer embodiment 1-2.

Embodiment 2-1

Adding 1 mol R-(−)-3-hydroxybutyric acid, 10 mol methanol, 5.2 g catalyst p-toluenesulfonic acid (a mass ratio of R-(−)-3-hydroxybutyric acid is 0.15%, and a water-carrying agent n-hexane with an amount of 50% of the alcohol volume in a three-necked flask; stirring and slowly increasing a temperature to 150° C., then keeping the temperature and reacting for 8 h; cooling to a room temperature after reaction is stopped; removing the remaining alcohol and n-hexane by vacuum distillation at 90° C. and 5000 Pa; increasing the temperature to 150° C., and collecting fraction under reduced pressure of <1000 Pa, wherein the fraction is 3-hydroxybutyrate methyl ester, and a yield is 93%.

Embodiments 2-2 to 2-8

On the basis of the embodiments 2-1, the embodiments 2-2 to 2-8 change methanol into ethanol, 1-propanol, 1-butanol, 1-pentanol, 1-hexanol, 1-heptanol and 1-octanol respectively, while other conditions are the same as those of the embodiment 2-1, so as to obtain R-(−)-3-hydroxybutyrate ethyl ester (yield 95%), R-(−)-3-hydroxybutyrate propyl ester (yield 93%), R-(−)-3-hydroxybutyrate butyl ester (yield 92%), R-(−)-3-hydroxybutyrate pentyl ester (yield 94%), R-(−)-3-hydroxybutyrate hexyl ester (yield 96%), R-(−)-3-hydroxybutyrate heptyl ester (yield 95%), and R-(−)-3-hydroxybutyrate octyl ester (yield 94%), wherein gas phase detection purity is about 100%.

Figure 3:
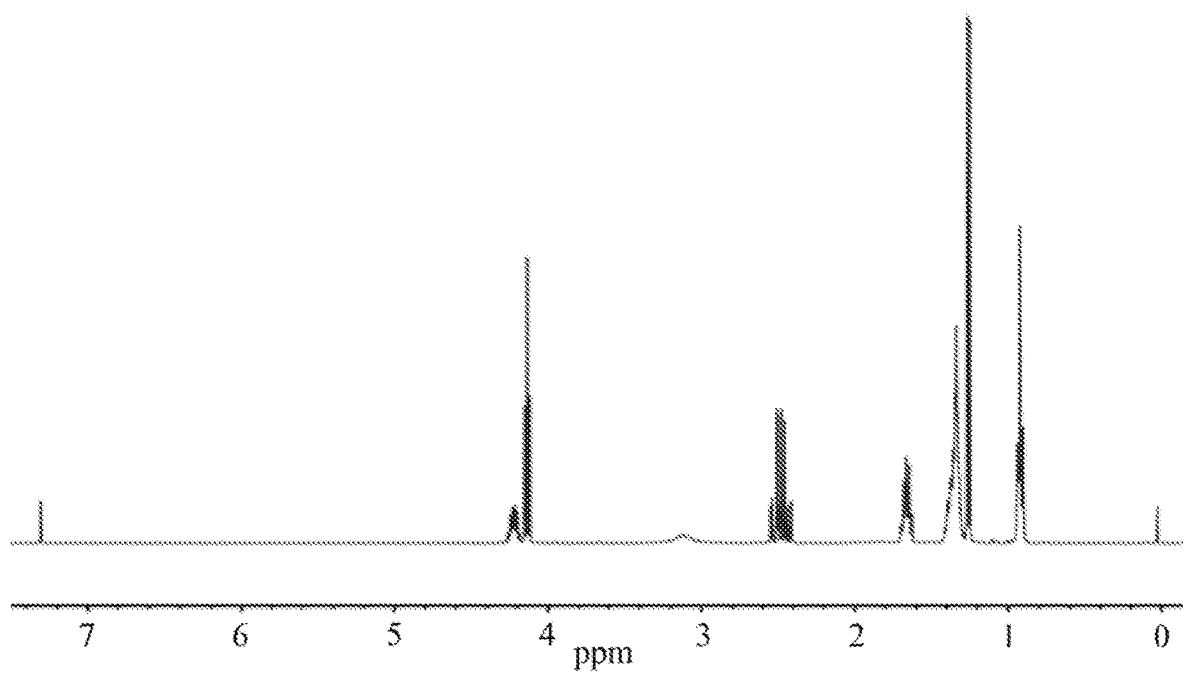
FIG. 3 is a nuclear magnetic spectrum of R-(-)-3-hydroxybutyrate hexyl ester.

FIG. 3 is a nuclear magnetic spectrum of R-(−)-3-hydroxybutyrate hexyl ester.

The R-(−)-3-hydroxybutyrate ethyl ester oligomer and R-(−)-3-hydroxybutyrate hexyl ester oligomer prepared in the embodiments 1-2 and 2-6 are tested by Guangdong Detection Center of Microbiology by referring to: Chinese Ministry of Health 2002 *"Disinfection Technical Specifications"*-2.1.8.4 *Minimum Inhibitory Concentration Test (Nutrition Broth Method)*, results are shown in Table 2.

TABLE 2

Minimum inhibitory concentration of different strains of R-(−)-3-hydroxybutyrate ethyl ester oligomer and R-(−)-3-hydroxybutyrate hexyl ester oligomer

| Sample | | Test microbial strain | Minimum inhibitory concentration (mg/kg) |
|---|---|---|---|
| Embodiment 2-6 | R-(−)-3-hydroxybutyrate ethyl ester oligomer | *Escherichia coli* 8099 | 1:256 |
| | | *Staphylococcus aureus* ATCC 6538 | 1:512 |
| | | *Pseudomonas aeruginosa* ATCC9027 | 1:2 |
| | | *Bacillus subtilis* var.nier ATCC 9372 | 1:512 |
| | | *Candida albicans* ATCC 10231 | 1:512 |
| | | *Aspergillus niger* ATCC 16404 | 1:1024 |
| Embodiment 1-2 | R-(−)-3-hydroxybutyrate hexyl ester oligomer | *Escherichia coli* 8099 | 1:64 |
| | | *Staphylococcus aureus* ATCC 6538 | 1:64 |
| | | *Pseudomonas aeruginosa* ATCC9027 | 1:32 |
| | | *Bacillus subtilis* var nier ATCC 9372 | 1:32 |
| | | *Candida albicans* ATCC 10231 | 1:32 |
| | | *Aspergillus niger* ATCC 16404 | 1:64 |

Embodiments 2-9

On the basis of the embodiment 2-1, R-(−)-3-hydroxybutyric acid is changed to R-(−)-3-hydroxypropionic acid, and methanol is changed to 1-hexanol. Other experimental conditions are the same as those of the embodiment 2-1 to obtain R-(−)-2-hydroxypropionic hexyl ester.

Figure 4:
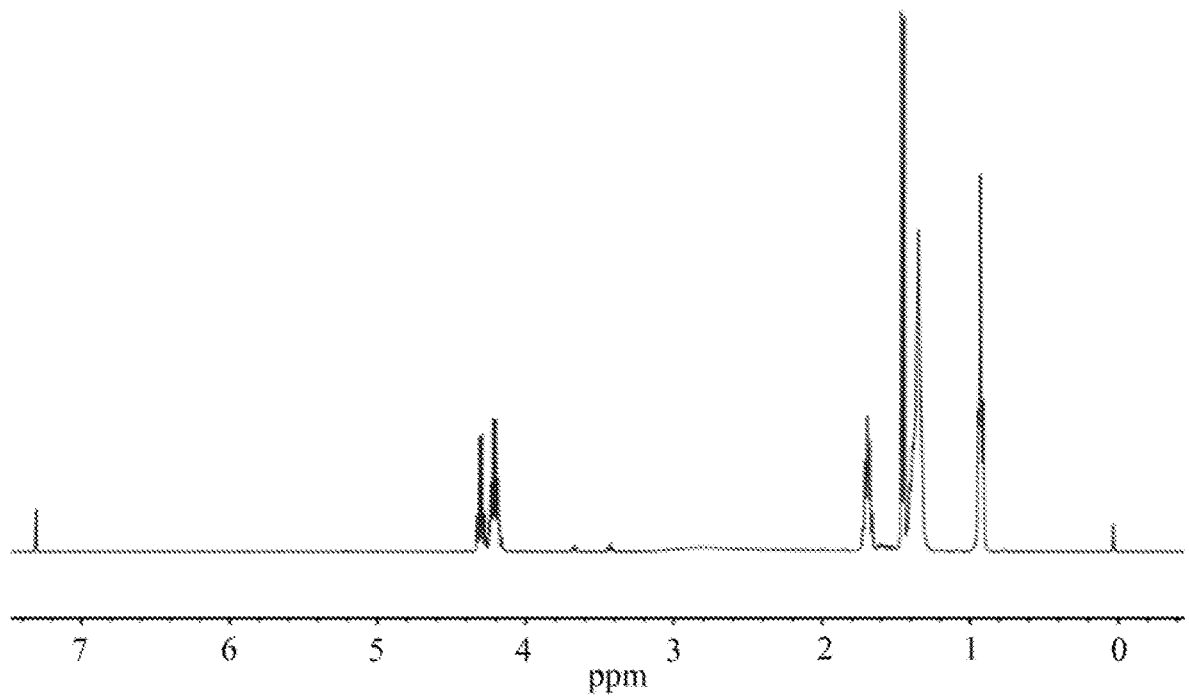
FIG. 4 is a nuclear magnetic spectrum of R-(-)-2-hydroxypropionic hexyl ester.

FIG. 4 is a nuclear magnetic spectrum of R-(−)-2-hydroxypropionic hexyl ester.

R-(−)-3-hydroxybutyric methyl ester NMR experimental data and spectra are assigned as follows: $^1$H NMR (CDCl$_3$): 4.33 (m, H), 3.72 (s, 3H), 2.53 (q, 2H), 1.21 (D, 3H)

R-(−)-3-hydroxybutyrate ethyl ester NMR experimental data and spectra are assigned as follows: $^1$H NMR (CDCl$_3$): 4.33 (m, H), 4.01 (m, 2H), 2.41 (m, 2H), 1.15 (M, 6H)

R-(−)-3-hydroxybutyrate propyl ester NMR experimental data and spectra are assigned as follows: $^1$H NMR (400 MHz, Chloroform-d) δ 4.28-4.16 (m, 1H), 4.10 (t, 2H), 2.59-2.40 (m, 2H), 1.76-1.64 (m, 2H), 1.26 (dd, 3H), 0.97 (t, 3H).

R-(−)-3-hydroxybutyrate butyl ester NMR experimental data and spectra are assigned as follows: $^1$H NMR (400 MHz, Chloroform-d) δ 4.48-4.39 (m, 2H), 4.33 (ddt, 4H), 2.78-2.55 (m, 4H), 1.84 (tdd, 4H), 1.69-1.52 (m, 4H), 1.49-1.39 (m, 6H), 1.21-1.09 (m, 6H).

R-(−)-3-hydroxybutyrate pentyl ester NMR experimental data and spectra are assigned as follows: $^1$H NMR (CDCl$_3$): 4.23 (m, H), 4.14 (t, 2H), 2.43 (m, 2H), 1.67 (M, 2H), 1.37 (m, 4H), 1.26 (d, 3H), 0.95 (m, 3H).

R-(−)3-hydroxybutyrate hexyl ester NMR experimental data and spectra are assigned as follows: $^1$H NMR (400 MHz, Chloroform-d) δ 4.29-4.18 (m, 1H), 4.14 (t, 2H), 2.58-2.40 (m, 2H), 1.73-1.61 (m, 2H), 1.44-1.29 (m, 6H), 1.26 (d, 3H), 0.97-0.89 (m, 3H).

R-(−)-3-hydroxybutyrate heptyl ester NMR experimental data and spectra are assigned as follows: $^1$H NMR (400 MHz, Chloroform-d) δ 4.23 (dqd, 1H), 4.14 (t, 2H), 2.53 (dd, 1H), 2.50-2.40 (m, 1H), 1.67 (t, 2H), 1.43-1.29 (m, 9H), 1.27 (dd, 3H), 0.92 (t, 3H).

R-(−)-3-hydroxybutyrate octyl ester NMR experimental data and spectra are assigned as follows: $^1$H NMR (400 MHz, Chloroform-d) δ 4.23 (t, 1H), 4.15 (t, 3H), 2.54 (dd, 1H), 2.46 (dd, 1H), 1.74-1.62 (m, 3H), 1.42-1.24 (m, 18H), 0.92 (t, 4H).

Embodiment 3: Synthesis of R-(−)-lactate Monomer (n=1)

Embodiment 3-1

R-(−)-3-hydroxybutyric acid in the embodiment 2-1 is changed to R-(−)-lactic acid, and methanol is changed to 1-hexanol. Other conditions are the same as those of the embodiment 2-1 to obtain R-(−)-lactate hexyl ester, wherein a yield is 94%, and a gas phase detection purity is about 100%.

Embodiments 3-2 to 3-3

On the basis of the embodiment 3-1, the embodiments 3-2 and 3-3 change 1-hexanol to ethanol and 1-heptanol respectively, and other conditions are the same as those in the embodiment 3-1 to obtain R-(−)-lactate ethyl ester and R-(−)-lactate heptyl ester, wherein gas phase detection purity is about 100%.

Embodiment 4: Synthesis of R-(−)-2-hydroxypropionate Hexyl Ester

On the basis of Embodiment 3-1, R-(−)-lactic acid is changed to R-(−)-2-hydroxypropionic acid to obtain R-(−)-2-hydroxypropionic hexyl ester, wherein a gas phase detection purity is about 100%.

R-(−)-2-hydroxypropionic hexyl ester NMR experimental data and spectra are assigned as follows: $^1$H NMR (CDCl$_3$): 4.29 (m, H), 1.60 (m, 2H), 1.42 (m, 9H), 0.88 (m, 3H).

Anti-bacterial tests and c log P theoretical calculation are performed on the products of the embodiment 2 and the embodiment 3, as shown in Table 3.

TABLE 3 anti-bacterial experimental data of hydroxy acid ester oligomers

| Name | Minimum inhibitory concentration MIC (mg · mL$^{-1}$) | Minimum inhibitory concentration MIC (agar method) | clogP |
|---|---|---|---|
| R-(−)-3-hydroxybutyric methyl ester | 62.50 | 10% | −0.16 |
| R-(−)-3-hydroxybutyrate ethyl ester | 31.25 | 5% | 0.37 |
| R-(−)-3-hydroxybutyrate propyl ester | 15.63 | 2% | 0.89 |
| R-(−)-3-hydroxybutyrate butyl ester | 7.81 | 1% | 1.42 |
| R-(−)-3-hydroxybutyrate pentyl ester | 3.91 | 0.5% | 1.95 |
| R-(−)3-hydroxybutyrate hexyl ester | 1.95 | 0.25% | 2.48 |
| R-(−)-3-hydroxybutyrate heptyl ester | 31.25 | >15% | 3.01 |
| R-(−)-3-hydroxybutyrate octyl ester | 31.25 | >20% | 3.54 |
| R-(−)-lactate ethyl ester | 35.55 | 5.25% | 0.33 |
| R-(−)-lactate hexyl ester | 1.95 | 0.25% | 2.44 |
| R-(−)-lactate heptyl ester | 28.56 | 4.38% | 2.97 |

Remarks: clogP represents the logarithmic value of the distribution coefficient of the substance in the two phases of fat and water. The data is theoretically estimated by using the ChemDraw Ultra 13.0 program; the basis and method of the anti-bacterial test method: Chinese Ministry of Health 2002 "Disinfection Technical Specifications"-2.1.8.4 Minimum Inhibitory Concentration Test (Nutrition Broth Method), the strain is *Escherichia coli* ATCC25922.

It can be seen from Table 2 that the c log P value of the hydroxy acid ester oligomers prepared by the present invention increases regularly with the chain length of the ester groups, but when the c log P value is about 2.4, the anti-bacterial effect is the highest (MIC is 1.95 mg/mL). Therefore, when c log P=2.4, the molecular size of R-(−)-hydroxy acid ester is the most suitable, which means it can be inserted into the cell membrane, destroy the stable structure of the cell membrane phospholipid bilayer, thereby achieving high anti-bacterial efficiency.

It should be noted that the specific embodiments described above do not constitute a limitation on the protection scope of the present invention. Any other corresponding changes and modifications made according to the technical concept of the present invention should be included in the claimed protection scope of the present invention.

What is claimed is:

1. A method of killing bacteria, comprising contacting the bacteria with an anti-bacterial compound, wherein the anti-bacterial compound is a water-insoluble substance of formula (I):

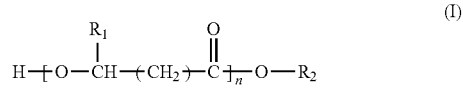

wherein n is a natural number of 4-8, R$_1$ is a C$_1$-C$_5$ alkyl group, R$_2$ is a C$_2$-C$_8$ alkyl group, and m is a natural number of 0-3.

2. A method of killing bacteria, comprising contacting the bacteria with an anti-bacterial compound, wherein the anti-bacterial compound is a water-soluble substance of formula (IV):

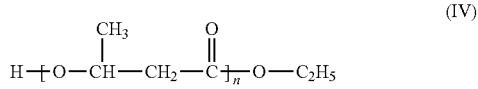

wherein n=2-3.

3. A method of killing bacteria, comprising contacting the bacteria with an anti-bacterial compound, wherein the anti-bacterial compound is a water-soluble substance of formula (V):

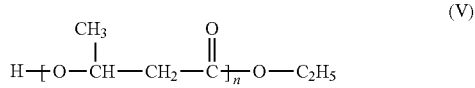

wherein n=4-8.

* * * * *